US006647298B2

(12) United States Patent
Abrahamson et al.

(10) Patent No.: US 6,647,298 B2
(45) Date of Patent: Nov. 11, 2003

(54) IMPLANTABLE MEDICAL DEVICE WITH VARIABLE INCOMING COMMUNICATION SIGNAL DISCRIMINATION, AND METHOD FOR OPERATING SAME

(75) Inventors: Hans Abrahamson, Stockholm (SE); Magnus Lindberg, Sundbyberg (SE)

(73) Assignee: St. Jude Medical AB, Järfälla (SE)

(*) Notice: Subject to any disclaimer, the term of this patent is extended or adjusted under 35 U.S.C. 154(b) by 183 days.

(21) Appl. No.: 09/873,909

(22) Filed: Jun. 4, 2001

(65) Prior Publication Data

US 2002/0183806 A1 Dec. 5, 2002

(51) Int. Cl.[7] .............................. H04B 5/02; G08C 17/00
(52) U.S. Cl. ................................. 607/60; 607/31
(58) Field of Search ............................. 607/60, 32, 31, 607/30, 34; 128/903, 901

(56) References Cited

U.S. PATENT DOCUMENTS 4,550,732 A * 11/1985 Batty et al. ................... 607/31
5,324,315 A * 6/1994 Grevious ..................... 607/60
5,683,432 A   11/1997 Goedeke et al.
6,201,993 B1  3/2001 Kruse et al.
6,556,871 B2 * 4/2003 Schmitt et al. ............... 607/60

* cited by examiner

Primary Examiner—Kennedy Schaetzle
(74) Attorney, Agent, or Firm—Schiff Hardin & Waite

(57) ABSTRACT

An implantable medical device communication unit bi-directionally communicates with an external device. The communication unit includes a receiver arranged to receive communication signals, having a signal strength, from the external device. The receiver includes a discriminator that is provided with a discriminator threshold such that the receiver means only accepts received signals having a signal strength higher than said discriminator threshold to activate the medical device. The discriminator threshold is adapted to be adjusted in response to control signals from a control unit in the medical device.

26 Claims, 2 Drawing Sheets

IMPLANTABLE MEDICAL DEVICE WITH VARIABLE INCOMING COMMUNICATION SIGNAL DISCRIMINATION, AND METHOD FOR OPERATING SAME

BACKGROUND OF THE INVENTION

1. Field of the Invention

The present invention relates to an implantable medical device, a communication method used in an implantable medical system, and an implantable medical system.

2. Description of the Prior Art

In RF coupled systems, which are perhaps the most commonly employed communication systems in modern implantable device systems, information is transferred from a transmitting coil to a receiving coil via a radio-frequency carrier signal. The carrier signal is modulated with the data that are to be transmitted using an appropriate modulation scheme, such as phase shift keying (PSK), frequency shift keying (FSK), or pulse position modulation (PPM), among numerous others. The modulated carrier induces a voltage in the receiving coil that tracks the modulated carrier signal. This received signal is then demodulated in order to recover the transmitted data. Because the stainless steel or titanium can commonly used to hermetically enclose an implanted device acts as a low-pass filter for the transmitted RF signals, attenuation increases as frequency is increased. Devices currently on the market have a maximum frequency of less than 200 kHz. Also, the transmitting range has been limited to 50 to 100 mm or so.

Depending upon the type of modulation and demodulation used in an RF communication system, the data or bit rate cannot exceed a predetermined fraction of the carrier frequency; otherwise, the ability to reliably distinguish between modulation representing a digital (binary) "1" from a digital "0" is compromised. Techniques are known which encode digital data to transmit more data per unit time and reduce implanted device current drain. However, at very high data transmission rates, the current drain would be very high.

RF communication programming units typically interface with the implanted device through the use of a programming head or programming paddle, a handheld unit adapted to be placed on the patient's body over the implant site of the patient's implanted device. In some cases, a magnet in the programming head effects closure of a reed switch in the implanted device to initiate a communication session (this is a safeguard against accidental programming of the device; otherwise, closure of the reed switch has little meaning as far as communication of information). Thereafter, uplink and downlink communication takes place between the implanted device's transmitter and receiver and a receiver and transmitter disposed within the programming head.

An implanted medical device, IMD, that utilizes so-called long range telemetry for bi-directional communication with an external telemetry device may suffer from too frequent, and also unwanted, activation of the telemetry receiver. Long range telemetry is herein defined as telemetry performed at a maximal distance between the implanted device and the sending unit of the external device of approximately 0.5 m up to 2 m.

The IMD receiver electronics must periodically, or continuously, "listen" for attempts made from the surrounding environment to establish contact over the communication channel. In order to be able to communicate over longer distances, the IMD receiver must be made rather sensitive. One consequence of making the IMD receiver rather sensitive is that it will thus respond to signals not necessarily intended for the implanted device. Nevertheless the electronics must be alert, decode the signals or noise and cannot revert to an idle state until it has made the decision whether the received signal was aimed for the device or not. Activating the entire chain of the receiver electronics now and then significantly increases the battery drain.

U.S. Pat. No. 5,683,432 discloses an adaptive, performance-optimizing communication system for communicating with an implanted medical device. In the system signals are transmitted and received in accordance with predetermined, interrelated operational parameters, such as transmission rate, transmitter power, and the like. Various aspects of system performance, including bit error rate in received signals, the strength of received signals, the signal-to-noise ratio of received signals, the presence of local RF noise and non-telemetry related RF signals, and the like, are dynamically monitored by the communication system, to determine whether predetermined system performance goals are being met. If it is determined that one or more system performance goals are not being met, one or more operational parameters may be automatically adjusted so that desired performance can be achieved.

U.S. Pat. No. 6,201,993 discloses a medical device for detecting an RF signal transmitted between an implantable medical device and an external medical device programmer in a telemetry session. In order to avoid transient and steady state noise in the RF signal transmitted uplink, i.e. from the implantable medical device to the external device, the receiver section of the external device is provided with an adaptive comparator circuit for comparing a demodulated uplink signal amplitude with an adaptive threshold signal. A receiver output signal is generated when the demodulated uplink signal amplitude exceeds the adaptive threshold amplitude of the adaptive threshold signal.

There are two main situations where long range telemetry is particularly useful.

The first situation is during implantation of the medical device where it is difficult to perform telemetry due to the requirements of keeping a sterile environment close to the patient.

The second situation is when a patient performs a follow up at home having the external device communicating to the physician e.g. via the telephone line. It is sometimes considered cumbersome to have to hold the telemetry head close to the skin. If instead it were possible to e.g. sit on a sofa up to e.g. 2 meters from the telemetry head the follow up would be much easier to perform.

None of the above discussed known techniques are directed to any of the problems related to long range telemetry.

SUMMARY OF THE INVENTION

An object of the present invention is to be able to control the remote accessibility of an implanted device and prevent external units from starting a bi-directional communication session without letting the IMD wearer being aware.

Further objects of the present invention are to reduce the power consumption caused by overly frequent receiver activation as well as to reduce unintentional access of an implanted device, especially when performing long range telemetry.

The above objects are achieved in accordance with the principles of the present invention in an implantable medical device, and a method for operating such a device, wherein the implantable medical device includes circuitry that requires activation by an activation signal in order to operate, and wherein a telecommunication unit is provided for bi-directional communication with an external device, the telecommunication unit including a receiver which receives communication signals, including an activation signal, from the external device, and having a discriminator, with a variable discriminator threshold, the discriminator allowing the activation signal to proceed to the receiver only if the signal strength of the activation signal exceeds the discriminator threshold, and wherein a control unit is provided that is connected to the discriminator, the control unit emitting control signals to the discriminator to set the discriminator threshold to a selected level.

An advantage obtained by the present invention is the increased communication safety achieved by making the discriminator threshold adjustable. Although the lowest threshold level is denoted "long range threshold" in practice the communication is often performed by having the external transmitting means arranged close to the skin of the patient. However, by using the present invention a higher safety is achieved when performing communication at a close distance. At the same time the communication system is quite insensitive to situations that intentionally or unintentionally may occur if the sending antenna of the external device is moved a bit farther away from the patient.

A further advantage of the present invention is it reduces the battery drain because the entire receiver electronics need not be activated during periods of noise.

In theory, of course it is possible that an IMD communication channel may be opened by simply increasing the transmitter energy from the external device, regardless of the distance between the IMD and the external device. However, in practice, the available frequency bands granted by the telecommunication authorities are restricted in use with respect to the emitted power within the bands.

DESCRIPTION OF THE PREFERRED EMBODIMENTS

Figure 1:
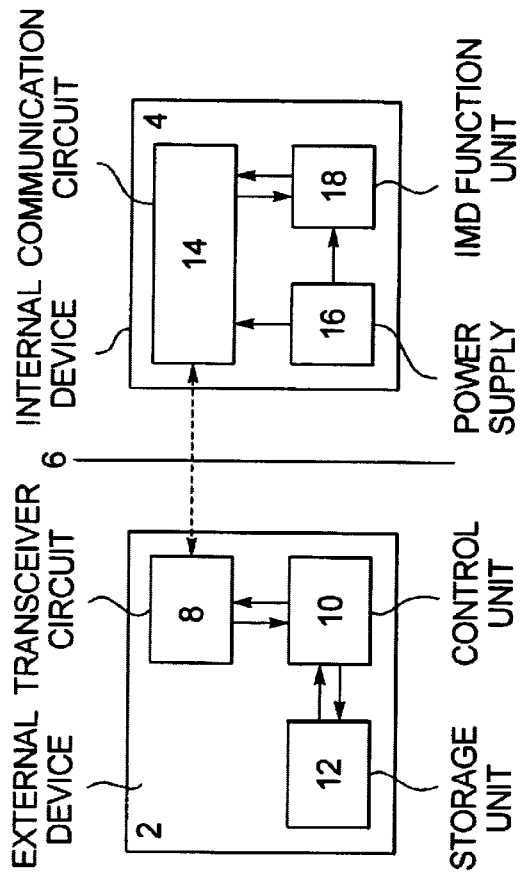
FIG. 1 is a simplified block diagram of a medical communication system according to the present invention.

The medical communication system shown in FIG. 1 has two devices, one of which is adapted to be implanted in a human or animal body. FIG. 1 shows a system having an external device 2 and an internal or implanted device 4 separated by the skin 6 of the patient. The external device 2 has a transmitter and receiver (transceiver) circuit 8, a control unit 10 and a storage unit 12. Naturally many other components are contained in the external device, but these are omitted for describing the present invention, as they are not directly involved in the operation of the invention. Those skilled in the art are aware of these other compounds, among which can be an energy source, a display, a data entry unit e.g. a keyboard, etc. Also omitted is a programming head, which inter alia includes a transmitting antenna, e.g. transmitting coils, used to generate the radio frequency signals. The programming head is connected to the external transceiver circuit 8 via e.g. a wireless connection, using inter alia Bluetooth protocol, or via an electrical cable, and is positioned during transmission e.g. on the skin close to the implanted device 4.

Any conventional programming head adapted for radio frequencies may be used.

The internal device 4 is adapted to be implanted into a human or animal body and contains an internal communication circuit 14 (a transceiver) arranged to communicate with the external transceiver circuit 8. The internal communication circuit 14 is provided with all necessary components in order to be able to perform the communication, e.g. a transmitting antenna, modulation and demodulation stages. The communication circuit 14 is described in detail with reference to FIG. 2. The internal device contains a power supply 16 and an implantable medical device function unit 18.

The internal device 4 may be any device adapted to be implanted into a human or animal body, e.g. a heart pacemaker, a heart defibrillator, a cardioverter or an infusion pump, and is naturally provided with the necessary means needed to perform its intended purpose. In the case of a heart pacemaker the internal unit includes pulse generator, an electrode, a control unit etc. The functional unit 18 generally performs the intended functions of the medical device.

In FIG. 1 the dotted double-arrowhead line designates the wireless (e.g. radio) frequency communication signal between the units.

Figure 2:
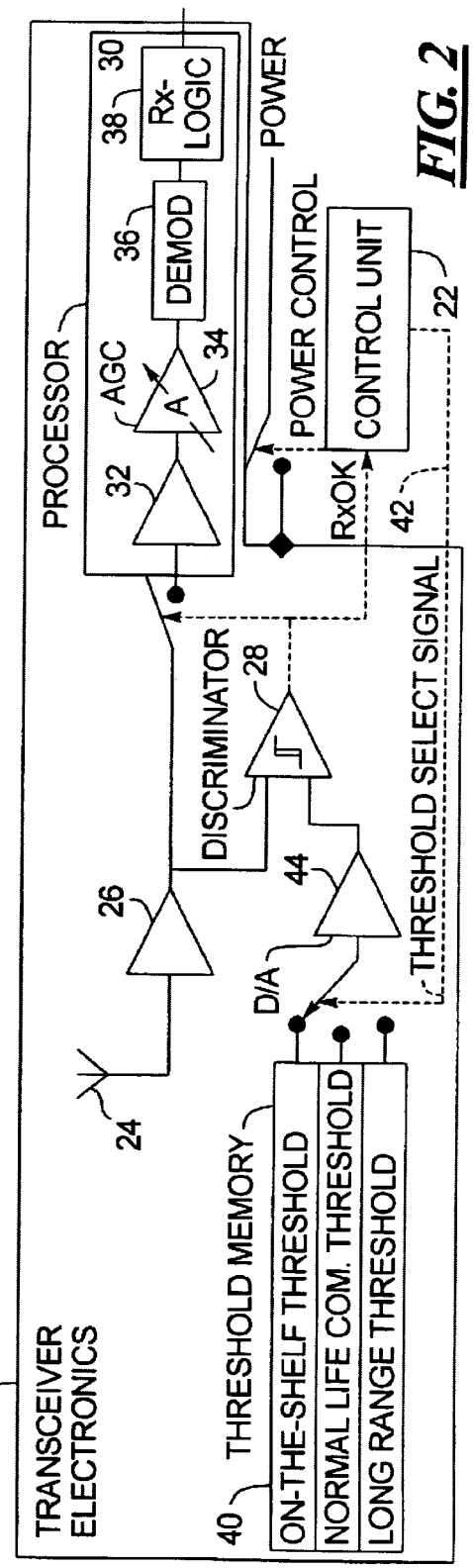
FIG. 2 is a block diagram of the communication circuitry according to the present invention.

With references to FIG. 2 the communication circuitry will be described in detail.

The communication circuit 14 has transceiver electronics 20 and a control unit 22.

The different circuitry arranged in the communication circuit 14 that will be disclosed below is primarily directed to circuitry involved when receiving signals from an external device. In order to achieve bi-directional communication with the external device the communication circuit 14 naturally also includes a transmitting circuit which, for sake of clarity, are described herein.

The transceiver circuit 20 has an IMD antenna 24 connected to a preamplifier 26. The output signal from the preamplifier 26 is applied to a discriminator 28 and via a switch to a signal processor 30. The signal processor 30 includes an amplifier 32, an automatic gain control (AGC) circuit 34, a demodulation circuit 36 and receiver logic 38. The transceiver circuit 20 further includes a threshold memory 40 controlled by the control unit 22 by a threshold select signal 42, and a digital to analog converter (D/A) 44 which converts the digital threshold value stored in the memory 40 into an analog value that is supplied to the discriminator 28. The output from the discriminator 28 is used to control the switch prior the processor 30 and is also applied to the control unit 22.

In the threshold memory 40 threshold values representing different thresholds are stored. FIG. 2 schematically illustrates only three different thresholds. The "on the shelf" threshold being a very high threshold used prior to implantation, the "adjusted normal life communication" threshold, being the threshold determined by the threshold test, and the "long range" threshold being used during follow-up sessions. The threshold memory 48 is arranged to store threshold values between the lowest threshold (long range threshold) up to the highest threshold (on the shelf threshold) in a number of steps, e.g. between 32 to 64 different steps. The threshold is selected by the threshold select signal 42 generated by the control unit. Thus, the threshold memory 40 stores the number of different threshold levels to be stored, i.e. at least two, reserves places in the memory for each threshold level and stores each threshold level value at its designated place.

The transceiver electronics receives power, generated by the power supply, via a switch that is controlled by a power control signal from the control unit.

The discriminator 28 generates an output signal if the applied received signal strength exceeds the discriminator threshold used for the moment. The signal strength may be determined by integrating the signal during a predetermined time interval, e.g. from approximately 1 µs up to 10 ms. The exact duration of the time interval is dependent of the used signal modulation method and in some cases even a time interval longer than 10 ms may be used, e.g. when On Off Keying (OOK) is used.

Another way to determine the signal strength is to use the peak amplitude of the received signal during the above mentioned time interval.

Figure 3:
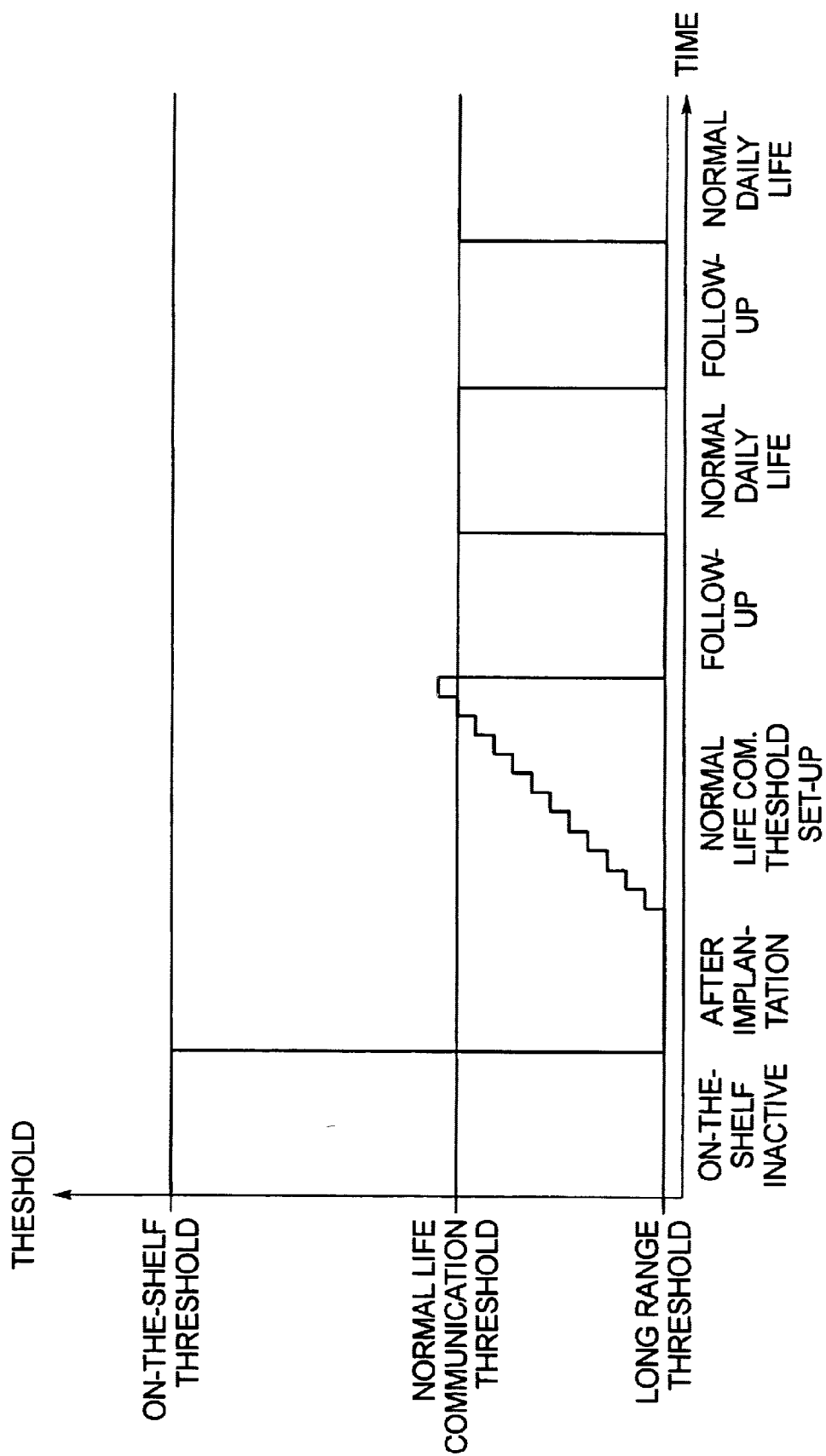
FIG. 3 is a graph that schematically illustrates the different threshold levels used, with respect to time.

FIG. 3 discloses a graph that schematically illustrates the different threshold levels used with respect to time.

To avoid overly frequent activation of the receiver electronics in a long-range telemetry system, the discriminator 28 is used in the receiver that only will allow signals at an energy level higher than a predetermined threshold to activate the system. The energy level is determined by performing measurements during a predetermined time period.

The discriminator 28 is thus provided with a discriminator threshold that is adjustable so that communication can be controlled differently in different situations.

As an example, the discriminator threshold is normally set high to make the system insensitive to communication attempts when a communication dialog with the implanted device not is intended to be established. This threshold is called normal communication threshold and is the threshold the discriminator 28 is provided with during normal daily life function of the implanted device 4.

If an interrogation is desired the external transmitter must be held close to the IMD to ensure that the normal life communication threshold of the receiver is exceeded and the receiver then is activated.

Thus, when a communication has been initiated in a proper way, which is detected by the discriminator 28 the control unit sets the discrimination threshold to the long range threshold, via the threshold select signal, to allow communication over longer distances.

In a preferred embodiment the following occurs if the communication channel unintentionally goes down during a session. The discrimination threshold then remains low for a predetermined period, e.g. 5 seconds up to e.g. 1 minute, to allow the communication to reestablish. If the communication has not re-established when the regain period has elapsed, the discrimination threshold is reset to the normal life communication threshold value in order to make the receiver insensitive.

The discriminator 28 may be designed to work either on the carrier frequency level or on an intermediate frequency.

The inventive method for controlling the activation threshold is advantageous not only when the device 4 is implanted in a body, but also when the device is still stored on the shelf. In the latter case, the sensitivity is set extremely low, i.e. the discrimination threshold is set extremely high, at the time of manufacture and the device 4 can communicate only over short distances, e.g. 10 cm in free air, as indicated in the left part of the graph in FIG. 3.

The on the shelf threshold level of the discrimination threshold may be lowered automatically or in response of specific command initiated from the external device 2 by a user.

In another embodiment of the invention the sensitivity is automatically set high (discrimination threshold is set low) once a pacing electrode is connected to the device 4, to allow communication over the maximum range.

In order to prevent the high "on-the-shelf" discriminator threshold level from being unintentionally set, that level may be disabled once the device is implanted, and is then no longer programmable by any means.

Using the adjustable normal life communication threshold not only will limit the number of receiver activation and save battery power but also will prevent the user from undesired access and a potential risk of detrimental actions.

The radio signal from the external device 2 to the implanted device 4 is attenuated during its propagation through skin, fatty tissue and muscles. It is therefore necessary for the normal life communication threshold to be adjustable in order to allow for different settings with respect to the communication sensitivity for a slim or an obese patient.

The actual separation between the implant 4 and an external transceiver placed directly on the skin surface can vary over a wide range from patient to patient. The signal decay due to the separation distance is approximately proportional to $1/r^3$ and an additional factor must be added due to the tissue dependent attenuation.

Once the medical device 4 has been implanted, the device's discrimination threshold is made adjustable to limit the initial communication range to e.g. approximately 25 cm. This is essential not only because individual settings between different patients are necessary but also because a patient can put on weight during the lifetime of the IMD.

The normal life communication threshold may be checked and perhaps adjusted e.g. at predetermined intervals, e.g. once every year, during the normal follow up procedure.

To achieve this flexibility, the external device 2 is provided with a special set-up program application that can be run after the implantation or at follow-up. When adjusting the normal life communication threshold, either the implanted device 4 (see first preferred procedure below) or the external device 2 (see second preferred procedure below) is the master that controls the set-up procedure.

The first preferred procedure for determining an normal life communication threshold set-up is controlled autonomously by the implantable medical device 4. This first procedure includes the following steps:

1. Place the external transceiver antenna 30 cm right in front of the patient and perpendicular to the implanted medical device 2.
2. Start the external device routine "Normal Life Communication Threshold Set-Up".
3. The routine sends a command to the IMD that starts an initial sensitivity level seek loop that further on will be controlled from the IMD.
4. The external device 2 continuously sends a training message at its maximum output energy level and waits for a respond from the IMD.
5. The IMD now gradually increases the discrimination threshold step by step until it cannot detect the training message signal from the external device 2.
6. The IMD saves the discrimination threshold in the internal memory and sends an "End of Normal Life Communication Threshold Set-Up" message to the external device 2 to terminate the application.
7. The IMD reverts to the previously used sensitivity level used before the Set-Up sequence was run if the follow up session is to be continued. When the follow up session is terminated the threshold is set to the newly determined normal life threshold.

In a second preferred procedure the set-up sequence allows the external device 2 to take control and send new threshold data to the implanted device 4. Starting at the long range threshold level, the external device will send new higher threshold data until the IMD no longer can detect the signal and replies with an end of set-up message. This second procedure includes the following steps:

1. Place the external transceiver antenna 30 cm right in front of the patient and perpendicular to the implanted medical device 4.
2. Start the external device routine "Normal Life Communication Threshold Set-Up".
3. The external device 2 sends commands with new sensitivity threshold data to the IMD. The first command contains a low discrimination threshold and, if received correctly, the IMD responds with acknowledge in order to confirm the transmission. The external device 2 shall send at its maximum output energy level.
4. The preceding commands contains threshold data that gradually increases the discrimination threshold in the IMD receiver means until the IMD cannot detect the signal from the external device 2 and will thus cease to acknowledge the commands.
5. The IMD saves the discrimination threshold in the internal memory and sends an "End of Normal Life Communication Threshold Set-Up" message to the external device to terminate the application.
6. The IMD reverts to the previously used sensitivity level used before the Set-Up sequence was run if the follow up session is to be continued. When the follow up session is terminated the threshold is set to the newly determined normal life threshold.

The normal life communication threshold test procedure is arranged to determine a normal life communication threshold adapted to be used during normal daily life of the patient being at the level where unintentional activation of the implanted medical device is avoided but ensuring that intentional activation is easily performed.

Thus, the test procedure includes a step of gradually, step-by-step, increasing the discriminator threshold until the signal strength no longer is higher than the threshold.

If, during the test procedure, the contact between the implanted medical device 4 and the external device 2 is lost the test procedure is terminated after a preset time, e.g. 5 seconds up to 1 minute. The test procedure also may be terminated if the normal life threshold is determined to be an unrealistically high value that exceeds a threshold that may be set to e.g. 50% of the on the shelf threshold value.

The above-described test procedures according to the first and second embodiments of the invention may be altered by, instead of increasing the discrimination threshold in the IMD receiver, the discrimination threshold starts at the highest threshold an decreases until the IMD detects the signal from the external device 2. When performing the test procedure according to this alternative embodiment, the system (the IMD and the external device) has a stored test procedure time, i.e. a maximal duration for the test procedure. If this test procedure time lapses, the connection is considered lost and the test procedure is terminated.

According to a preferred embodiment of the present invention, in order to further reduce the power needed in the IMD transceiver system, the control unit 22 will only power up the transceiver electronics during short sniff intervals e.g. 10–20 milliseconds every two second. The control unit 22 controls, via the power control switch, the power to the transceiver. If the received signal has a signal strength high enough to pass the discriminator threshold, the control unit 22 detects this by receiving an RxOK signal from the discriminator 28 and leaves power on to make the device try to detect the entire expected message.

According to another preferred embodiment of the present invention, in order to be able to save even more power, the received signal is only connected via the switch to the power consuming intermediate amplifier 32, the automatic gain control (AGC) amplifier 34, the demodulator 28 and the receiver logic 38 in the signal processor means 30 if the discriminator 28 has accepted the signal level in the first stage.

According to a preferred embodiment of the present invention two requirements must be fulfilled in order to initiate a telemetry communication session. The first requirement is that the signal strength must exceed the current discrimination threshold, most often the normal life communication threshold. The second requirement is that the received signal contains the "Open Channel" message. If the signal contains the correct "Open Channel" message, the device 4 will enable the "long range threshold" to allow communication from a more remote position. Alternatively, the external device 2 has to initiate the long-range mode by sending a command to switch the acceptance threshold and make the receiver sensitive to low signal levels.

In the present application the preferred embodiments of the invention are described by giving examples of telemetry communication performed by using radio frequency communication telemetry. Those persons skilled in the art of telemetry communication to medical implantable devices are aware of many other techniques to perform telemetry communication. Among those are inductive communication telemetry and by optical communication telemetry. Thus, the present invention is equally applicable with any known telemetry technique.

Although modifications and changes may be suggested by those skilled in the art, it is the intention of the inventor to embody within the patent warranted hereon all changes and modifications as reasonably and properly come within the scope of his contribution to the art.

We claim:

1. An implantable medical device comprising:
   circuitry requiring activation by an activation signal in order to operate;
   a telemetry communication unit adapted for bi-directional communication with an external device, said telemetry communication unit including a receiver adapted to receive communication signals, including said activation signal, from the external device, said communication signals each having a signal strength, and a discriminator preceding said receiver and having a variable discriminator threshold, said discriminator allowing said activation signal to proceed to said receiver only if the signal strength of said activation signal exceeds said discriminator threshold; and
   a control unit connected to said discriminator which emits control signals to said discriminator to set said discriminator threshold to a selected level.

2. An implantable medical device as claimed in claim 1 wherein said control unit generates control signals to respectively set said discriminator threshold between a high threshold prior to implantation and a low threshold after implantation.

3. An implantable medical device as claimed in claim 1 wherein said receiver comprises a threshold memory, connected to said discriminator, for storing at least two different values of said discriminator threshold, and wherein said control signals from said control unit respectfully select one of said different values from said threshold memory for use by said discriminator.

4. An implantable medical device as claimed in claim 1, wherein said receiver comprises an integrator for integrating said activation signal to determine the signal strength thereof for comparison to said discriminator threshold.

5. An implantable medical device as claimed in claim 1, wherein said receiver comprises an amplitude identifier which identifies a peak signal amplitude of said activation signal, as an indicator of the signal strength of the activation signal, for comparison to said discriminator threshold.

6. An implantable medical device as claimed in claim 1, wherein said control unit generates said control unit to set said discriminator threshold in a threshold test wherein said receiver is adapted to receive a test signal which is used to set said discriminator threshold.

7. An implantable medical device as claimed in claim 6 wherein, during said threshold test, said control unit generates control signals to increase said discriminator threshold in successive steps until the signal strength of said test signal is not higher than said discriminator threshold.

8. An implantable medical device as claimed in claim 1 wherein said receiver is connected between said discriminator and said circuitry, and wherein said implantable medical device comprises a power source for supplying power to said receiver via a power control switch operated by said control unit and wherein said discriminator supplies a signal to said control unit instructing said control unit to close said power control switch only when said signal strength of said activation signal exceeds said discriminator threshold.

9. An implantable medical device as claimed in 1 wherein said telemetry communication unit is adapted for bi-directional radio frequency communication with the external device.

10. An implantable medical device as claimed in 1 wherein said telemetry communication unit is adapted for bi-directional inductive communication with the external device.

11. An implantable medical device as claimed in 1 wherein said telemetry communication unit is adapted for bi-directional optical communication with the external device.

12. An implantable medical device as claimed in claim 1 wherein said telecommunication unit requires receipt of an "open channel" message from the external unit to be received among the communication signals by said receiver in order to establish bi-directional communication with the external device.

13. A method for activating circuitry in an implanted medical device requiring an activation signal in order to operate, comprising the steps of:
   placing an external device in proximity to said implanted medical device and transmitting said activation signal from said external device to said implanted medical device, said activation signal having a signal strength;
   in said implantable medical device, comparing the signal strength of the activation signal to a variable discriminator threshold and allowing said activation signal to proceed to said circuitry, to activate said circuitry, only if said signal strength of said activation signal exceeds said discriminator threshold; and
   in said implantable medical device, setting said variable discriminator threshold to a selected level dependent on a usage status of said implantable medical device.

14. A method as claimed in claim 13 comprising varying said discriminator threshold between a high level prior to implantation and a low level after implantation.

15. A method as claimed in claim 13 comprising a plurality of different levels for said discriminator threshold in a memory in said implantable medical device, and retrieving one of said stored levels from said memory for comparison with said signal strength of said activation signal dependent on said usage status.

16. A method as claimed in claim 13 comprising identifying said signal strength of said activation signal by integrating said activation signal in said implanted medical device.

17. An implantable medical device as claimed in claim 13 comprising identifying said signal strength of said activation signal in said implantable medical device by identifying a peak signal amplitude of said activation signal during a predetermined time.

18. A method as claimed in claim 13 comprising the additional steps of conducting a threshold test and in said threshold test transmitting a training message from said external device to said implanted medical device and setting said discriminator threshold in response to said training message.

19. A method as claimed in claim 18 comprising, in said threshold test, increasing said discriminator threshold successively in steps until said signal strength of said activation signal is not higher than said discriminator threshold.

20. A method for operating a medical communications system including an external device and an implanted medical device, said implanted medical device containing circuitry requiring an activation signal in order to operate, said method comprising the steps of:
   establishing communication between said external device and said implanted medical device;
   executing a computer program routine in said external device having a threshold level seek loop;
   while executing said computer program routine, continuously transmitting from said external device a training message at a maximum output energy level and waiting at said external device for a response from said implanted medical device;
   in said implantable medical device, gradually changing a discrimination threshold in successive steps until a change in detection of said training message signal occurs; and
   storing a highest discrimination threshold in said implanted medical device at which said training message was detected, and using the stored discrimination threshold for receiving subsequent communications signals from said external device; and
   terminating said threshold level seek loop in said external device.

21. A method as claimed in claim 20 wherein the step of establishing communication between said external device and said implanted medical device comprises places an external transceiver antenna of said external device in front of a patient in whom said implanted medical device is implanted, and orienting said antenna substantially perpendicularly to said implanted medical device.

22. A method as claimed in claim 20 wherein the step of gradually changing said discrimination threshold comprises gradually increasing said discrimination threshold until said training message is not detected.

23. A method as claimed in claim 20 wherein the step of gradually changing said discrimination threshold comprises gradually decreasing said discrimination threshold until said training message is detected.

24. A method as claimed in claim 20 comprising, in said subsequent communication, resetting said discrimination threshold to a long range threshold level for conducting a follow-up session, and otherwise maintaining said threshold at said stored threshold.

25. A medical communication system comprising:

an external device having a transmitting antenna and a signal generating circuit which generates communication signals, including an activation signal;

an implanted medical device containing circuitry requiring activation by said activation signal in order to operate;

said implanted medical device further containing a telemetry communication unit for receiving said communication signals from said antenna of said external device, said communication signals, including said activation signal, having a signal strength;

a discriminator in said telemetry communication unit having a variable discrimination threshold, said discriminator comparing said signal strength of said activation signal to said discrimination threshold and allowing said activation signal to proceed to said circuitry requiring activation only if the signal strength of the activation signal exceeds said discrimination threshold; and a control unit is said implantable medical device connected to said discriminator which emits control signals to said discriminator to set said discrimination threshold to a selected level.

26. A medical communication system as claimed in claim 25 wherein said signal generating circuit in said external device executes a computer program routine to continuously emit a training message, while said control unit in said implanted medical device is gradually changing said discrimination threshold until a change in detection of said training message occurs, and wherein said implantable devices comprises a memory for storing a highest threshold at which detection of said training message occurred.

* * * * *